Figure 1:
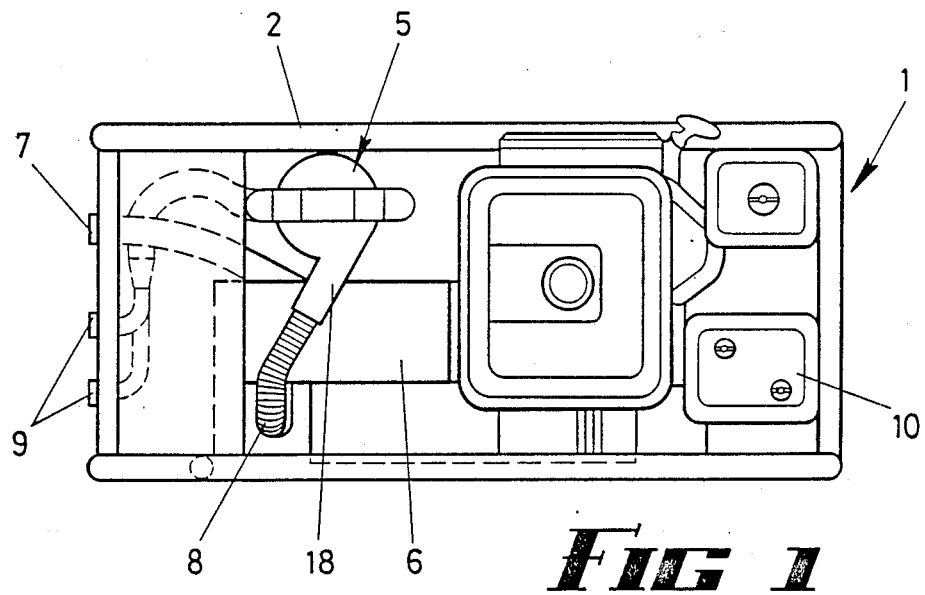

United States Patent [19]

Atkinson et al.

[11] Patent Number: 4,922,651
[45] Date of Patent: May 8, 1990

[54] APPARATUS FOR EFFECTING OR IMPROVING POLLINATION OF PLANTS

[75] Inventors: Donald T. Atkinson; Dianne L. Atkinson, both of Whakatane, New Zealand

[73] Assignee: DFC New Zealand Limited, Wellington, New Zealand

[21] Appl. No.: 125,254

[22] Filed: Nov. 25, 1987

[30] Foreign Application Priority Data

Nov. 28, 1986 [NZ] New Zealand ............... 218444
Jun. 5, 1987 [NZ] New Zealand ............... 220593

[51] Int. Cl.⁵ .................... A01H 1/02; A01G 7/00
[52] U.S. Cl. .................................................. 47/1.41
[58] Field of Search ................ 47/1.41, 1.3, 1.5, 58

[56] References Cited

U.S. PATENT DOCUMENTS

| 2,477,947 | 8/1949 | Yadoff | 47/58 |
| 2,775,065 | 12/1956 | Chepil et al. | 47/1.41 |
| 3,558,052 | 1/1971 | Dunn | 239/124 X |
| 3,943,660 | 3/1976 | Hosaka | 47/1.41 |
| 4,087,937 | 5/1978 | Meador | 47/1.41 |
| 4,542,855 | 9/1985 | Stacey | 239/124 X |
| 4,751,791 | 6/1988 | Al-Rawi | 47/1.41 |

FOREIGN PATENT DOCUMENTS

| 550728 | 4/1932 | Fed. Rep. of Germany | 47/1.41 |
| 503818 | 12/1954 | Italy | 47/1.41 |
| 147392 | 10/1962 | U.S.S.R. | 47/1.41 |
| 375057 | 6/1973 | U.S.S.R. | 47/1.41 |
| 400287 | 3/1974 | U.S.S.R. | 47/1.41 |
| 677731 | 8/1979 | U.S.S.R. | 47/1.41 |
| 969212 | 11/1982 | U.S.S.R. | 47/1.41 |

Primary Examiner—Robert A. Hafer
Assistant Examiner—Kevin G. Rooney
Attorney, Agent, or Firm—Abelman Frayne Rezac & Schwab

[57] ABSTRACT

The method and apparatus described involves sucking pollen from male orchard plants and blowing the pollen onto selected female plants. The collected pollen is diverted through a separation device such as a cyclone where the pollen may be stored.

3 Claims, 6 Drawing Sheets

APPARATUS FOR EFFECTING OR IMPROVING POLLINATION OF PLANTS

This invention relates to methods of and apparatus for effecting or improving pollination of plants.

Inadequate pollination of plants is a problem for orchardists. Improved pollination increases yield whilst inadequate pollination increases costs because inadequately pollinated plants compensate with growth of extraneous matter.

Orchardists have relied on natural methods of pollination in the past. Kiwifruit orchardists for example rely on bees in the main although it is thought that other insects or winds may play a part in pollination. When a species has more than one type of flower honey bees can often distinguish between them and may only visit one type. This is the case with kiwifruit and as a result bees do not visit flowers randomly reducing the chances of successful pollination. To be successful an orchard needs to have adequate male vines distributed among the females and if bees are the main source of pollination then the orchardist needs to ensure that all female flowers receive muliple visits. In the kiwifruit industry the size of fruit is of concern to the grower because his payments are very much dependent upon this.

U.S. Pat. No. 4,087,937 discloses an apparatus for pollinating plants which is specifically adapted for use in relation adjacent rows of plants. This apparatus is not suitable for pollinating orchard plants such as kiwifruit and is also restricted to use with regular rows of plants.

It is an object of the present invention to provide a pollination apparatus for orchard plants where the plant flowers are some distance from the ground.

Further objects and advantages of the present invention will become apparent from the ensuing description which is given by way of example.

According to the present invention there is provided a method of pollination comprising the steps of
(a) selectively positioning a collection device adjacent male plants,
(b) sucking pollen from the male plants using an air suction device which is remote from said collection device and transferring the pollen to a holding device,
(c) dispersing the pollen from said holding device onto selected female plants.

According to a further aspect of the present invention there is provided an apparatus for improving or effecting pollination of plants said apparatus comprising a collection device communicable with a holding device, a suction device remote from and communicable with said collection device and a dispersal device communicable with said holding device, the arrangement and construction being such that on positioning said collection device adjacent a male flower pollen grain is drawn into the holding device and is collected and/or dispersed onto female flowers via said dispersal device.

Figure 2:
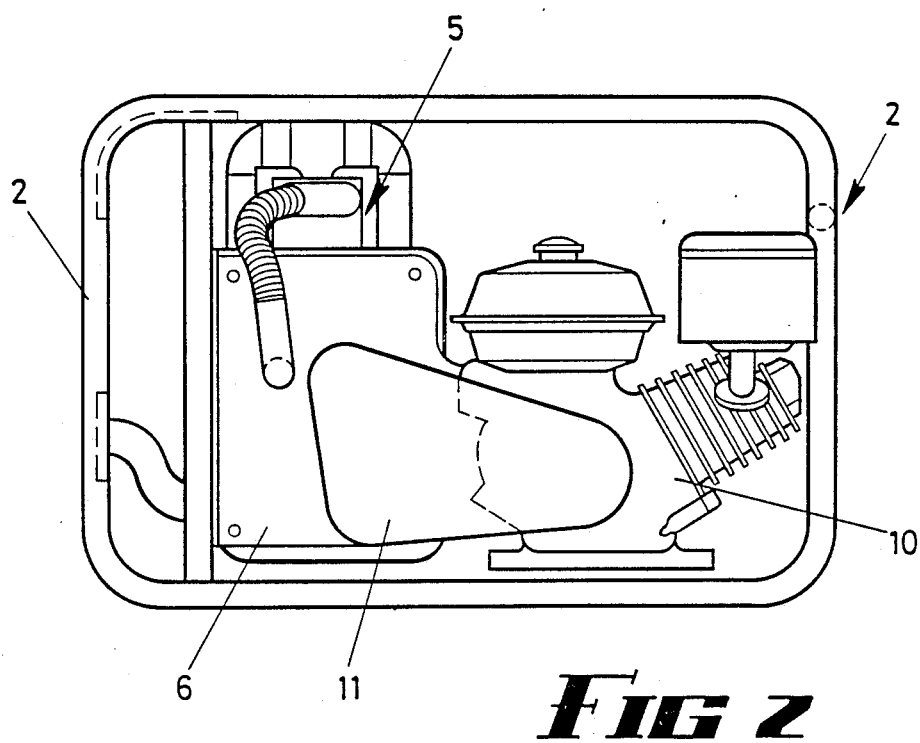
Figure 3:
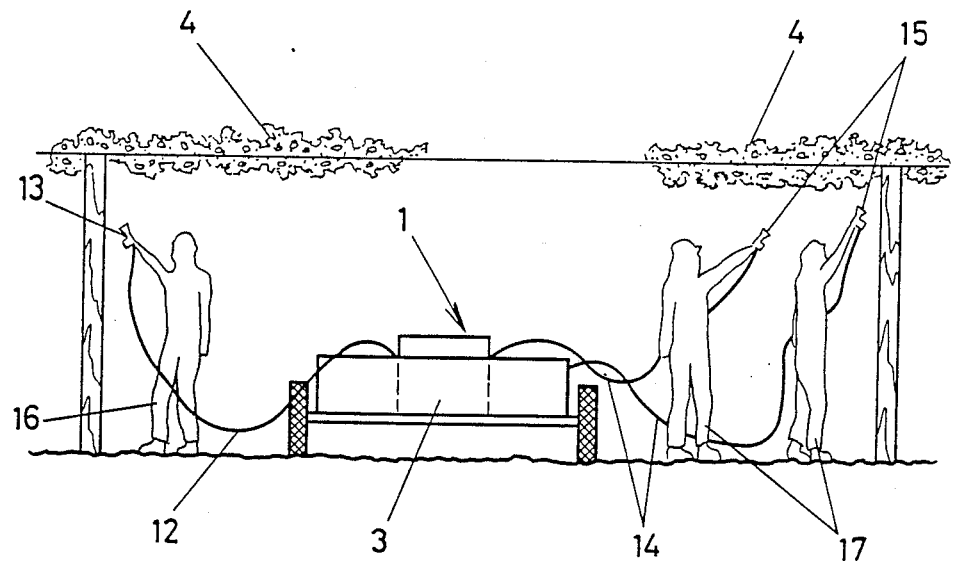
Figure 4:
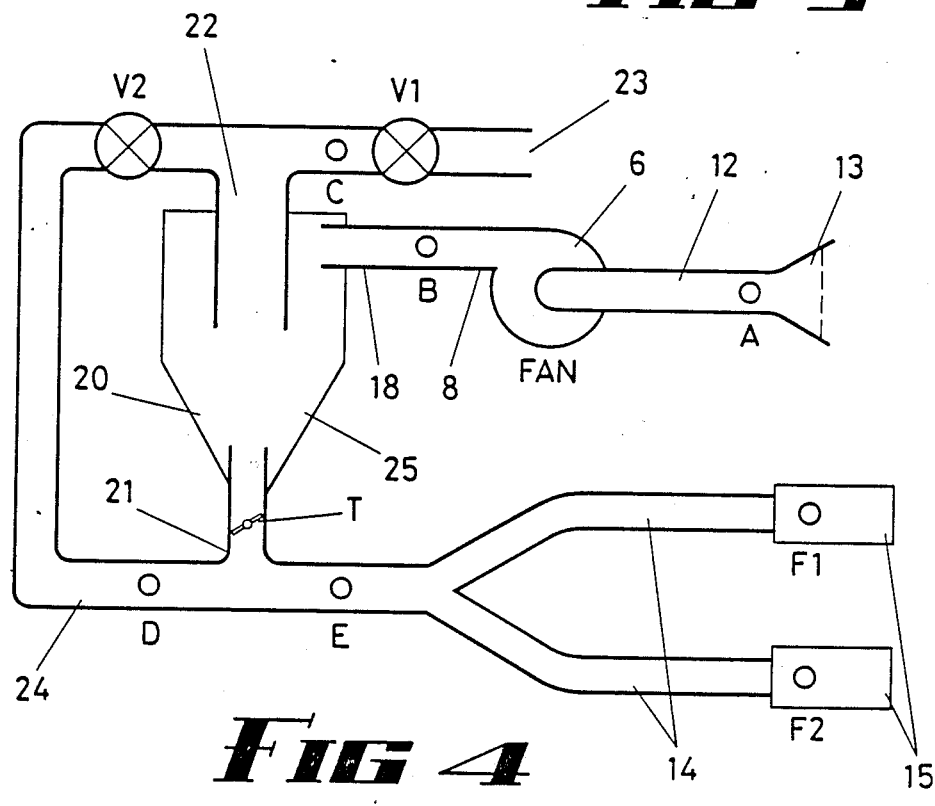
Figure 5:
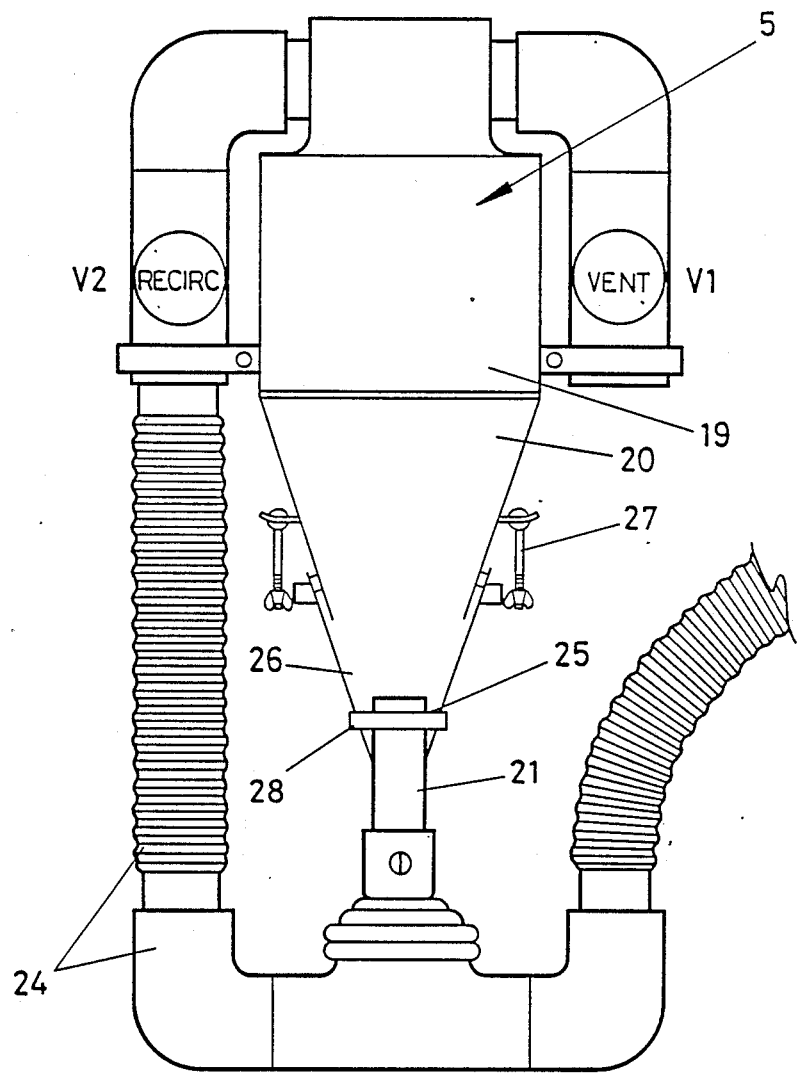
Figure 6:
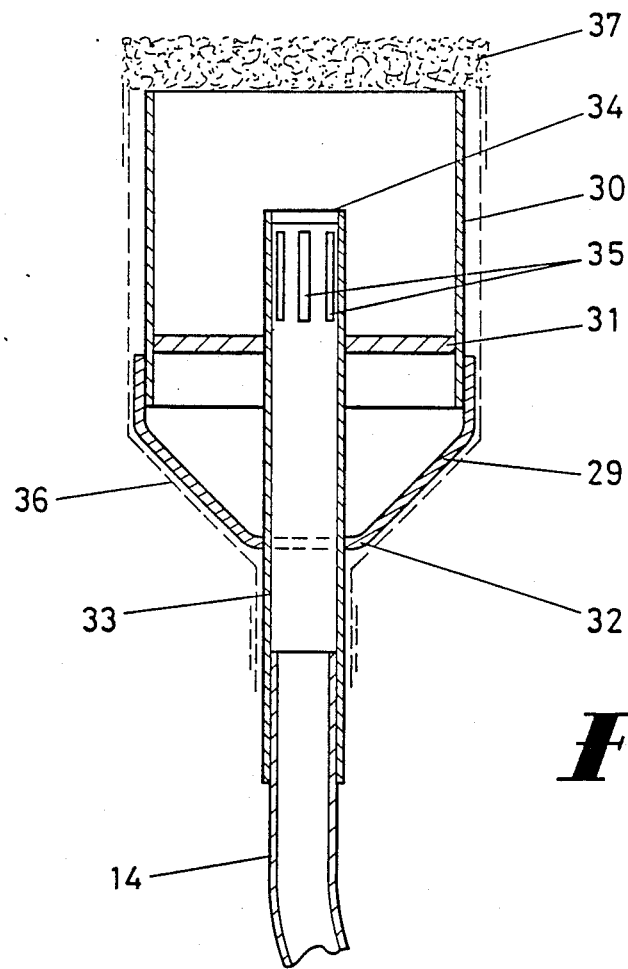
Figure 7:
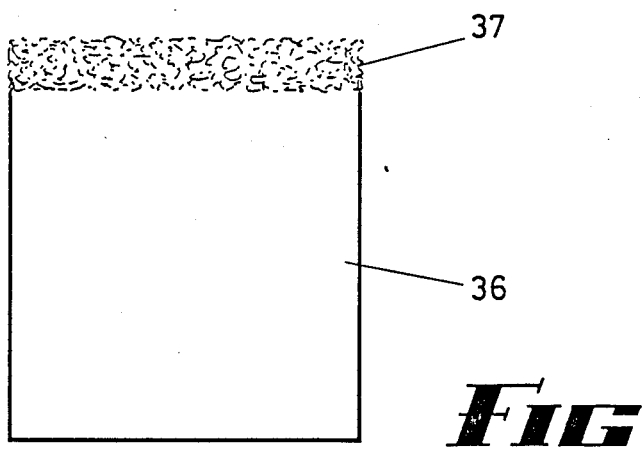
Figure 8:
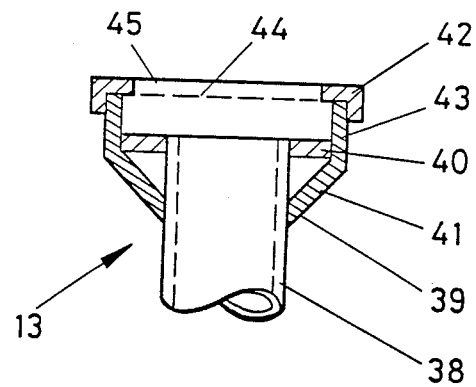
Figure 9:
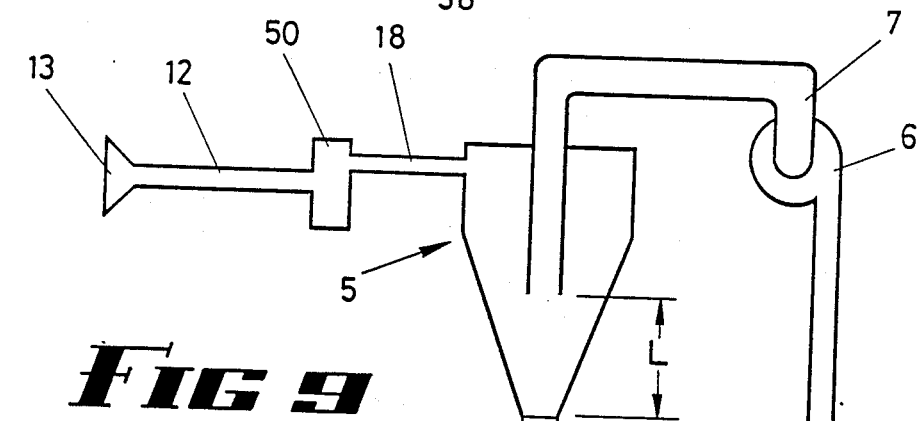
Figure 10:
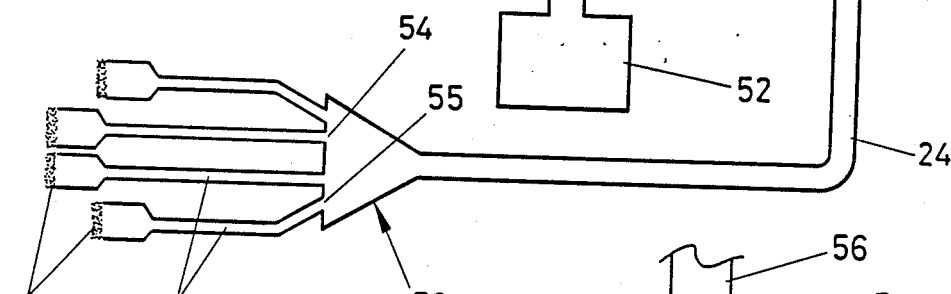
Figure 10:
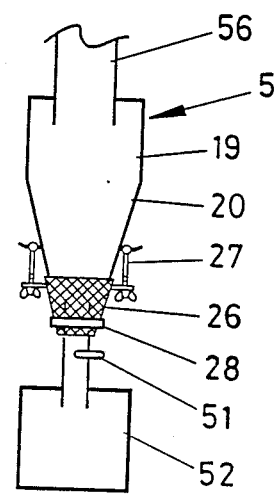

Aspects of the present invention will now be described by way of example with reference to the accompanying drawings in which:

FIGS. 1 and 2: are plan and side views respectively of a power unit and collection device for a pollination apparatus in accordance with the present invention, and FIG. 3: is a sketch showing how the pollination apparatus can be set up and used in an orchard, and FIG. 4: is a diagrammatic drawing which shows the principles of operation of a collection device in accordance with the present invention, and FIG. 5: is a side view of a collection device in accordance with one possible embodiment of the present invention, and FIG. 6: is a cross sectional drawing of a dispersal nozzle for a pollination apparatus in accordance with the present invention, and FIG. 7: is a side view of a filter sock for the nozzle of FIG. 6, and FIG. 8: is a diagrammatic sectional drawing of a nozzle for a collection device in accordance with the present invention, and FIG. 9: is a diagrammatic drawing which shows an alternative arrangement for the collection device, and FIG. 10: is a diagrammatic drawing showing the collection device including a pollen storage vessel at the base thereof.

With respect to the drawings pollination apparatus in accordance with the present invention comprises a portable power unit and collection device generally indicated by arrow 1 mounted on a frame 2. The power unit and collection device 1 may be mounted on a trailer or set up on the rear of a vehicle or have its own wheels (not shown), and in orchard situations can be transported between rows of vines 4 (FIG. 3). The collection device incorporates a cyclone unit generally indicated by arrow 5 and a fan 6. An inlet 7 is provided to the fan 6.

Two pollinator arrangements are illustrated diagrammatically by FIGS. 4 and 9 respectively. The FIG. 4 arrangement the cyclone 5 is communicable with exhaust 8 of the fan and the outlet 21 from the cyclone 5 is split into two branches 14. The inlet 7 is connected via a hose 12 to a collection nozzle 13 and the outlets 9 are connected via hoses 14 to dispersal nozzles 15. The alternative FIG. 9 arrangement is described later.

The power unit is a petrol motor 10 adapted to drive the fan 6 through a stepped up belt drive unit (not shown) which is housed within a cover 11. The motor 10 is a small petrol driven engine such as a 4-stroke Honda GX110 engine specified as having a maximum shaft speed of 3600 rpm.

The fan 6 can be a purpose made fan although other fans such as a Lamb two-stage fan may be used.

Single or two stage gearing between the motor output and the fan 6 can be used and an approximate gearing ratio six to one via a flat belt linkage is suitable.

One method of using the pollination apparatus is shown by FIG. 3. An operator 16 takes pollen from male flowers using the collection nozzle 13 whilst operators 17 disperse pollen grain to female flowers in the vicinity of the apparatus using nozzles 15.

The hoses 12 and 14 need to be flexible and have the capability of staying open without collapsing. A suitable hose is ribbed polyethylene hose sold under the name MASTERFLEX by Dunlop Flexible Hoses Limited. The first experimental pollination apparatus was designed for use in kiwifruit orchards and it was necessary to select a hose which minimizes airflow resistance and provides an operator with convenience in moving hoses around in orchards. Another consideration was to have an airflow which is sufficiently turbulent to avoid pollen disposition in the hoses and it was found that a hose internal diameter of 32 mm was a good choice, with the lengths of the hoses 12 and 14 being about 7 meters and 14 meters respectively.

The function of the cyclone 5 is to hold up movement of pollen grain between the time of intake and dispersal and to produce an even concentration of pollen. The cyclone is illustrated in more detail in relation to FIGS. 4 and 5 of the drawings. The fan 6 operates to suck pollen grain from male plants via the collection nozzle 13. The fan 6 delivers the pollen grain to cyclone 5 from where the grain suspended in air is delivered to female plants via the dispersal nozzles 15. The cyclone 5 is provided with a tangental entry 18, has an upper cylindrical body part 19 and a lower conical body part 20. The cyclone has a lower outlet 21 and an upper outlet 22. The upper outlet 22 is an exhaust outlet having a branch 23 to atmosphere and a second branch 24 which loops back to connect with the outlet 21. Valves V1 (a vent valve) and V2 (a recirculation valve) are interposed in the branches 23 and 24 respectively.

The cyclone 5 and the valves V1 and V2 are used to control the rate at which suspended pollen is dispersed in relation to its collection. There are two aspects to this control.

Firstly within the cyclone itself the outlet 21 is arranged to extend upwardly into the body of the conical part 20 to provide a trap 25 for pollen grains. The second aspect of control is in the use of the valves V1 (to exhaust) and the restriction valve V2 which is interposed in the branch 24.

The rate of flow of suspended pollen from the cyclone 5 is dependent on the size of the bottom outlet 21, the height to which this outlet protrudes into the cyclone body (and hence the volume of the trap 25) and the amount of pressure generated inside the cyclone by control of the valve V1.

Four adjustments for control are:
a. The protrusion height of the bottom outlet 21 into the cyclone 5. This controls the volume of pollen grain which may accumulate before it flows out.
b. The main exhaust valve V1 to waste. This partially controls the airflow through the valve V2 and the pressure within the cyclone.
c. The main exhaust valve V2 in the branch 24. This partially controls the airflow to the dispersal nozzles 15 and pressure within the cyclone 5.
d. A throttle T in the outlet 21. This partially controls the pressure in the cyclone.

The following represents probably the most appropriate pollinator conditions.

| Points of Measurement (see FIG. 4) | Pv mm water | Ps mm water | V m/s | Fl liters/sec |
|---|---|---|---|---|
| A | 66 | 104 | 33 | 21.7 |
| B | 40 | 480 | 26 | 20.6 |
| C | 8 | 155 | 11 | 8.9 |
| D | 4 | 18 | 8 | 6.5 |
| E | 7 | 16 | 11 | 8.6 |
| F | 2 | 5 | 6 | 4.6 |
| Pressure difference across fan: | | | | 703 |
| Pressure difference across cyclone: | | | | 325 |
| Flow through lower exit of cyclone: | | | | 2.1 |
| Ratio flow out:flow in | | | | 0.86 |
| Estimated error of flow results: | | | | ±2 m/s |

Pv Velocity pressure in mm water
Ps Static pressure in mm water
V Air velocity in m/s
Fl Air flow in liters/sec FIG. 5 of the drawings illustrates a cyclone construction. The cyclone 5 can be fabricated from a metal or plastics with a lower part 26 of the conical part 20 being constructed in a clear plastics so that an operator can see the amount of pollen which has accumulated in the trap 25. Adjustment nuts 27 are used to connect the lower part 26 to the conical part 20. It is preferable that the extent in which the outlet 21 protrudes into the lower part 26 of the cyclone is adjustable and this adjustment can be achieved by the positioning of an adjustment nut 28 fixed to the lower part 26 with respect to which a threaded exterior of the outlet 21 can be adjusted. The branches 23 and 24 can be constructed from standard PVC plumbing fittings and flexible hose.

The venting valve V1 and recirculation valve V2 are butterfly valves having control stems (not shown) which extend outside the fittings in which they are accommodated.

The dispersal nozzles 15 connected via hose 14 to the outlet from the cyclone are illustrated in a preferred form by FIGS. 6 and 7. The dispersal nozzles comprises a frustro-cone 29 mounting a pipe 30 a bulk head 31 and an aperture 32 in the cone 29 supports a tube 33 which extends into the nozzle and is connected to hose 14. The tube 33 has a cap 34 and a plurality of radially extending slits 35. FIG. 7 of the drawings illustrates a filter device which can be secured over each nozzle 15 (as is indicated by the broken line of FIG. 6) the filter comprising a cylindrical fabric body 36 which is complementary to the pipe 30 and cone 29 and a synthetic fur end cap 37. In operation suspended pollen delivered to the nozzle is dispersed via slits 35 and from the nozzle by passing through the fur section 37 of the filter. The filter becomes saturated with pollen.

FIG. 8 of the drawings illustrates a preferred construction for the collection device 13. The collection device can comprise a tube 38 supported by an aperture 39 and a bulk head 40 from a frustro cone 41, a cap 42 mounted about the peripheral lip 43 of the frustro cone 41 is used to secure a filter 44 over the entry 45 to the frustro cone 41.

FIG. 9 illustrates an alternative pollinator arrangement. In this arrangement a filter 50 is interposed between the collection nozzle 13 and the cyclone entry 18. The pump 6 is positioned between the cyclone 5 and the nozzles 15. The base of the cyclone 5 includes a bung or tap 51 which separates the cyclone from a collection bottle 52. The pump 6 is connected via branch 24 to a dispersal device generally indicated by arrow 53 which includes a splitter 54 and nozzles 14. The alternative cyclone construction is illustrated in more detail in relation to FIG. 10 of the drawings. Cyclone 5 has an upper cylindrical body part 19 and a lower conical body part 20. The cyclone also has an upper outlet 8 that leads to the air pump 6.

Cyclone 5 can be fabricated from a metal or plastics with a lower part 26 of the conical part 20 being constructed in a clear plastics so that an operator can see the amount of pollen which has accumulated in the trap 25. Adjustment nuts 27 are used to connect the lower part 26 to the conical part 20.

The tap 51 is opened when it is desired merely to collect pollen and not disperse it during collection.

The distance between the base of the cyclone outlet tube 56 and the bottom of the cyclone indicated by L can be varied and is proportional to the amount of disturbance of the pollen within the cyclone. The tube 56 can be secured in the desired position by simple means such as a thread and locking nut (not shown).

Once the pollen has been pumped to the dispersal device 53 it passes through a splitter 54. The splitter has the configuration of a truncated cone with the apex end connected to hose 24. At the base end of the splitter there are four equally spaced apertures 55 between which the pollen is divided on its way to the dispersal nozzles 15.

The four dispersal nozzles 15 ensure that an even distribution of the pollen occurs. In all other respects the FIG. 9 embodiment is the same as an uses similar components to that described in relation to FIG. 4.

The apparatus of FIGS. 1 to 8 is operated as follows:

The throttle of the motor 10 is set to give a fan speed of approximately 10,500 rpm corresponding to an air inlet flow of about 20 liters per second. Inlet hose 12 and outlet hoses 14 are connected as shown and these can be provided with sockets be or push friction fits.

The nut 28 at the base of the lower part 26 of the cone 20 is adjusted to protrude at approximately 5 mm above the bottom of the inside of the cone. The throttle T is left in a fully open position unless it is required to collect pollen without dispersal.

The vent valve V1 and recirculation valves V2 are set in a predetermined position from the fully open position. With the collection device clear of any dirt, sand or other debris the motor can be started and an air inlet flow of approximately 20 liters per second is set up by adjusting the motor speed with the air inlet flow being monitored by a pressure gauge (not shown). The vent and recirculation valves V1 and V2 are adjusted until an outlet flow of approximately 5 liters a second also monitored by a pressure gauge (not shown) is achieved. Such adjustments should be obtained using both the vent and recirculation valves V1 and V2. For any particular setting on the recirculation valve V2 the setting on the vent valve V1 has the effect of increasing outlet flows and increasing the pressure within the cyclone (causing pollen to pass to the exit air stream more rapidly and decreasing the average residence time of pollen in the cyclone). The volume of pollen grain held in the cyclone 5 at any given time is a matter to work out for individual conditions and can be controlled by the height of the outlet tube 21 protruding into the perspex cone. For low tube height in the cone there would be adequate build up of pollen to even out the flow of incoming pollen from the collection nozzle 13.

The best time to use the pollinator is at between 30% to 50% flowering, 60% to 80% of flowering and then at last flowering. It is best to choose a time when the flowers have no free water on them.

The operators 17 operating the dispersal nozzles 15 work systematically so that flowers are not missed and pause momentarily at each female flower which still has its petals offering up the distribution nozzle to touch the flower. Simultaneously the collection operator 16 could be collecting from as many male flowers as possible during the period. The collection nozzle should be dabbed at the male flowers so that anthas brush against the mesh filter. The mesh filter should be kept reasonably clean.

Experimental trials with the pollination apparatus have achieved significant results with yields increased from 30% to 50% by comparison with plans left to pollinate using natural methods.

The filter placement of a filter over the dispersal nozzle further improves pollination. The fur section 37 of the filter becomes saturated during use and pollen grains are carried to the female flowers suspended in air and in addition by touching the flowers with the pollen saturated filter. It may not be practical or desirable to use the filter under some circumstances. It may for example be better for the grower to pre-spray the plants with water prior to using the pollinator.

It will be apparent that the apparatus of the present invention can be used to collect pollen, to collect and simultaneously disperse the pollen or to disperse pollen. Where the apparatus is used to collect pollen, the branch 24 can be disconnected and a collection vessel such as a jar (not shown) connected to the outlet 21.

The apparatus may also be used to disperse pollen in a mist or water spray.

The alternative pollinator arrangement illustrated by FIGS. 9 and 10 simplifies operational procedures. Whilst throttling and control valves such as described in relation to the FIG. 4 arrangement can be incorporated in the alternative construction of FIG. 9. These are not essential for successful operation.

The use of a cyclone to separate the suspended pollen and its subsequent resuspension prior to dispersal has been found to electrostatically charge the pollen grains. The charge is a negative charge. This greatly enhances the adherence of the grain to the female flowers.

Aspects of the present invention have been described by way of example only and it will be appreciated that modifications and additions thereto may be made without departing from the scope of the invention defined in the appended claims.

We claim:

1. Apparatus for use in the pollination of female plant flowers comprising:
   a cyclonic separator for the separation of pollen particles from a forced flow of air through said separator;
   fan means associated with said separator and providing said forced flow of air through said separator;
   a hand-held collection nozzle connected to an air inlet of said cyclonic separator by a flexible conduit, said hand-held collection nozzle being randomly moveable by a person effecting collection of said pollen particles;
   a hand-held dispersion nozzle connected to an air outlet of said cyclonic separator by a flexible conduit, said hand-held dispersion nozzle being randomly moveable by a person effecting the pollination of said female plant flowers, and, controllable means for adjustably proportioning the amount of said pollen particles retained in said cyclonic separator and the amount of said pollen particles discharged from said cyclonic separator and entrained in said air flow outletting said cyclonic separator;
   whereby, said apparatus can be selectively employed for the collection of pollen particles, for the dispersion of pollen particles stored in said cyclonic separator, and, for the simultaneous collection of said pollen particles and the dispersion of at least a portion of said collected pollen particles.

2. The apparatus of claim 1, including a filtering device associated with said hand-held dispersion nozzle, said filtering device, during operation of the apparatus, becoming saturated with pollen particles and being usable for contact application of said pollen particles with randomly selected female flowers.

3. The apparatus of claim 2, including a sleeve which extends into said cyclonic separator and which ensures that an air pollen mixture is drawn from said cyclonic separator in a region above a pollen storage portion of said cyclonic separator located at the base of said cyclonic separator.

* * * * *